United States Patent
Saadeh

(10) Patent No.: US 10,426,744 B2
(45) Date of Patent: Oct. 1, 2019

(54) ANTI-FUNGAL COMPOSITIONS FOR TREATING NAILS AND METHODS FOR FABRICATING AND USING THEREOF

(71) Applicant: Harrow Health, Inc., San Diego, CA (US)

(72) Inventor: Dennis Elias Saadeh, Irvine, CA (US)

(73) Assignee: Harrow Health, Inc., San Diego, CA (US)

( * ) Notice: Subject to any disclaimer, the term of this patent is extended or adjusted under 35 U.S.C. 154(b) by 0 days.

(21) Appl. No.: 16/026,542

(22) Filed: Jul. 3, 2018

(65) Prior Publication Data

US 2018/0311188 A1   Nov. 1, 2018

Related U.S. Application Data

(63) Continuation-in-part of application No. 15/467,064, filed on Mar. 23, 2017, now abandoned.

(60) Provisional application No. 62/320,013, filed on Apr. 8, 2016.

(51) Int. Cl.

| | |
|---|---|
| *A61K 31/137* | (2006.01) |
| *A61K 31/4196* | (2006.01) |
| *A61K 31/4174* | (2006.01) |
| *A61P 31/10* | (2006.01) |
| *A61K 47/10* | (2017.01) |
| *A61K 47/12* | (2006.01) |
| *A61K 47/40* | (2006.01) |
| *A61K 9/06* | (2006.01) |
| *A61K 31/192* | (2006.01) |

(52) U.S. Cl.
CPC .............. *A61K 31/137* (2013.01); *A61K 9/06* (2013.01); *A61K 31/192* (2013.01); *A61K 31/4174* (2013.01); *A61K 31/4196* (2013.01); *A61K 47/10* (2013.01); *A61K 47/12* (2013.01); *A61K 47/40* (2013.01); *A61P 31/10* (2018.01); *A61K 2300/00* (2013.01)

(58) Field of Classification Search
CPC .............. A61K 31/4196; A61K 31/137; A61K 31/4174; A61K 9/0014; A61K 47/10; A61K 47/40; A61K 47/12; A61P 31/10
See application file for complete search history.

(56) References Cited

U.S. PATENT DOCUMENTS

| | | | | |
|---|---|---|---|---|
| 5,422,347 | A * | 6/1995 | Bononi | ................ A61K 31/415 514/58 |
| 2003/0235541 | A1* | 12/2003 | Maibach | .............. A61K 9/0014 424/61 |
| 2009/0202602 | A1* | 8/2009 | Ishima | ................. A61F 13/105 424/405 |
| 2016/0008295 | A1 | 1/2016 | Tseng et al. | |
| 2017/0290810 | A1* | 10/2017 | Saadeh | ............. A61K 31/4196 |

* cited by examiner

*Primary Examiner* — Theodore R. West
(74) *Attorney, Agent, or Firm* — Wagenknecht IP Law Group, PC

(57) ABSTRACT

Pharmaceutical compositions for treating, mitigating or preventing fungal nail diseases, disorders or pathologies are described, the compositions comprising at least one functionalized allylamine compound, at least one functionalized triazole compound, and at least one functionalized imidazole compound. Methods for fabricating the compositions and using them are also described.

15 Claims, No Drawings

ANTI-FUNGAL COMPOSITIONS FOR TREATING NAILS AND METHODS FOR FABRICATING AND USING THEREOF

CROSS-REFERENCE TO RELATED APPLICATION

This is a continuation-in-part application claiming the benefit of priority under 35 U.S.C. § 120 to U.S. application Ser. No. 15/467,064, filed Mar. 23, 2017, now pending, which claims priority under 35 U.S.C. § 119(e) to U.S. Provisional Application No. 62/320,013, filed Apr. 8, 2016, the entire content of each of which is hereby incorporated by reference.

FIELD OF THE INVENTION

The present invention relates generally to the field of dermatology and more specifically to compositions and methods designed to treat, mitigate or prevent fungal diseases, disorders and/or pathologies of nails, and to methods of preparing such compositions.

BACKGROUND

Fungal nail infections (also known as onychomycosis or tinea unguium) are very common for both fingernails and toenails, particularly frequently for the latter. Such infections often manifest themselves by the visible increase of the thickness and discoloration of the nail, with typical colors being white, black, or dark-yellow.

With the infection progressing, the skin can become inflamed and painful underneath and around the nail, particularly in the nailbed, and the nail can become brittle, with pieces breaking off the toe or finger, completely or partially, forming painful and esthetically unattractive patches, scaly skin, and the like. These disorders frequently cause a great deal of pain, discomfort, embarrassment, and other psychological and emotional problems to those who suffer from them. These disorders are often very difficult to treat or prevent.

Current pharmacological treatments include the use of topical or oral anti-fungal medications. All such treatments are beneficial but all are of limited effectiveness for many patients. Side effects are sometimes severe, and in general, treatment may present a serious challenge due to the infection being embedded within the nail and thus being difficult to reach. The treatment may be of a prolonged nature, and it may take a year or more for the course of treatment to be complete.

Accordingly, there exists a need to have better methods and compositions for treatment, mitigation and/or prevention of fungal diseases, disorders and/or pathologies of nails. This patent specification discloses such pharmaceutical compositions that would achieve positive patient outcomes while being free of drawbacks and deficiencies of existing formulations, and methods of fabricating and administering the same.

SUMMARY

According to one aspect of the invention, a pharmaceutical composition formulated in a form that is suitable for topical administration for treating, mitigating or preventing fungal nail diseases, disorders or pathologies is provided, the composition comprising, consisting essentially of, or consisting of a therapeutically effective quantity of an antifungal component consisting of at least one functionalized allylamine compound, at least one functionalized triazole compound, and at least one functionalized imidazole compound; a therapeutically effective quantity of at least one pharmaceutically acceptable penetration enhancing compound; and at least one pharmaceutically acceptable excipient.

According to various embodiments of the invention, the allylamine compound is terbinafine, amorolfin, flunarizine, naftifine, butenafine or a combination thereof, such as terbinafine.

According to various embodiments of the invention, the triazole compound is fluconazole, isavuconazole, itraconazole, terconazole, voriconazole, albaconazole, efinaconazole, epoxiconazole, propiconazole, ravuconazole, posaconazole or a combination thereof, such as fluconazole.

According to various embodiments of the invention, the imidazole compound is miconazole, ketoconazole, clotrimazole, sertaconazole, sulconazole, tioconazole, fenticonazole, isoconazole, bifonazole, econazole, omoconazole, luliconazole, butoconazole, oxiconazole, or a combination thereof, such as miconazole.

According to various embodiments, the compositions of the present invention are generally acidic and may have a pH ranging between about 2.0 and about 6.5, such as between about 2.5 and about 5.5, for example, between about 3.0 and 4.0. In various embodiments, the compositions of the present invention have a pH of about 4.0

According to yet another aspect of the invention, a method for treating, mitigating or preventing fungal nail diseases, disorders or pathologies is provided, comprising administering topically to a patient in need thereof a pharmaceutical composition, the composition comprising, consisting essentially of, or consisting of a therapeutically effective quantity of an antifungal component consisting of at least one functionalized allylamine compound, at least one functionalized triazole compound, and at least one functionalized imidazole compound; a therapeutically effective quantity of at least one pharmaceutically acceptable penetration enhancing compound; and at least one pharmaceutically acceptable excipient.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or biological compound or substance, or a mixture or combination of two or more such compounds or substances, intended for use in the medical diagnosis, cure, treatment, or prevention of disease or pathology.

The terms "anti-fungal" and "antimycotic" used herein interchangeably, refer to any substance or compound that destroys fungi and/or inhibits the growth thereof via any mechanism or route.

The term "allylamine" refers to the chemical compound 3-aminopropene having the following chemical formula: $CH_2=CH-CH_2-NH_2$ (those having ordinary skill in the art know that "allyl" is the following moiety: $CH_2=CH-CH_2-$), and the term "functionalized allylamine" refers to chemical compounds that are derived from allylamine, e.g., are obtained by substituting one or more hydrogen atoms in the structure thereof.

The term "terbinafine" (the regular IUPAC name is 6,6-dimethylhept-2-en-4-yn-1-yl](methyl)(naphthalen-1-ylmethyl)amine) refers to a functionalized allylamine having the following chemical structure:

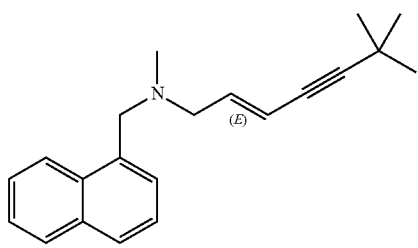 [SMILES: CN(C/C=C/C#CC(C)(C)C)Cc1cccc2ccccc12]

The tem "triazole compound" refers to chemical compounds that incorporate in their structure any heterocyclic structure having a five-membered ring of two carbon atoms and three nitrogen atoms (e.g., 1,2,4-triazole shown below):

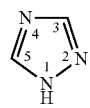

The term "fluconazole" (the regular IUPAC name is 2-(2,4-difluorophenyl)-1,3-bis(1H-1,2,4-triazol-1-yl)propan-2-ol) refers to a triazole compound having the following chemical structure:

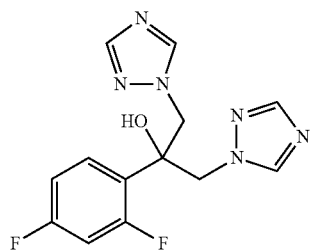 [SMILES: OC(Cn1cncn1)(Cn1cncn1)c1ccc(F)cc1F]

The term "imidazole compound" refers to chemical compounds that incorporate in their structure any heterocyclic structure having a five-membered ring of three carbon atoms and two nitrogen atoms (e.g., 1,3-diazole shown below):

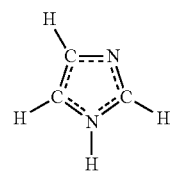

The term "miconazole" (the regular IUPAC name is 1-(2-(2,4-dichlorobenzyloxy)-2-(2,4-dichlorophenyl)ethyl)-1H-imidazole) refers to an imidazole compound having the following chemical structure:

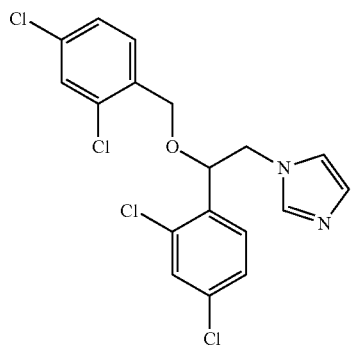 [SMILES: Clc1ccc(COC(Cn2ccnc2)c2ccc(Cl)cc2Cl)c(Cl)c1]

The term "penetration enhancing compound" refers broadly to any compound that increases the rate of topical delivery of an active compound from a pharmaceutical composition compared with the rate of delivery of the same active compound from a pharmaceutical composition having no such penetration enhancing compound.

The terms "onychomycosis" and "tinea unguium" refer to any fungal nail infection caused by any fungus (onychomycosis) or to dermatophyte nail infections only (tinea unguium).

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" is defined as a carrier, whether diluent or excipient, that is compatible with the other ingredients of the formulation and not deleterious to the recipient thereof.

The terms "administration of a composition" or "administering a composition" is defined to include an act of providing a compound of the invention or pharmaceutical composition to the subject in need of treatment.

B. Embodiments of the Invention

According to embodiments of the present invention, pharmaceutical compositions formulated in a form that is suitable for topical administration for treating, mitigating or preventing fungal nail diseases, disorders or pathologies are provided. The compositions of the present invention comprise, consist essentially of, or consist of therapeutically effective quantities of an antifungal component, a therapeutically effective quantity of at least one pharmaceutically acceptable penetration enhancing compound, and at least one pharmaceutically acceptable excipient.

The antifungal component comprises, consists of, or consists essentially of, the following three compounds. The first compound of the antifungal component comprises, consists of, or consists essentially of, one or more functionalized allylamine(s). The second compound of the antifungal component comprises, consists of, or consists essentially of, one or more functionalized triazole(s). The third compound of the antifungal component comprises, consists of, or consists essentially of, one or more and at least one functionalized imidazole(s).

The concentration of the antifungal component in the compositions of the present application may be between about 3.0 mass % and about 25.0 mass % of the total mass of the composition, such as between about 6.0 mass % and about 10.0 mass %, for example, about 8.0 mass %.

According to further embodiments, functionalized allylamine(s) that can be used for formulating the antifungal component include terbinafine, amorolfin, flunarizine, naftifine, butenafine, or a combination thereof. Those having ordinary skill in the art may select other functionalized allylamine(s) if desired, but may find that the use of the above-mentioned functionalized allylamine(s) such as terbinafine is particularly beneficial.

The concentration of the functionalized allylamine(s) in the antifungal component of the compositions of the present application may be between about 1.0 mass % and about 5.0 mass % of the total mass of the composition, such as between about 1.5 mass % and about 2.5 mass %, for example, about 2.0 mass %.

According to further embodiments, functionalized triazole(s) that can be used for formulating the antifungal component include fluconazole, isavuconazole, itraconazole, terconazole, voriconazole, albaconazole, efinaconazole, epoxiconazole, propiconazole, ravuconazole, posaconazole, or a combination thereof. Those having ordinary skill in the art may select other functionalized triazole(s) if desired, but may find that the use of the above mentioned functionalized triazole(s) such as fluconazole is particularly beneficial.

The concentration of the functionalized triazole(s) in the antifungal component of the compositions of the present application may be between about 1.0 mass % and about 10.0 mass % of the total mass of the composition, such as between about 3.0 mass % and about 5.0 mass %, for example, about 4.0 mass %.

According to further embodiments, functionalized imidazole(s) that can be used for formulating the antifungal component include miconazole, ketoconazole, clotrimazole, sertaconazole, sulconazole, tioconazole, fenticonazole, isoconazole, bifonazole, econazole, omoconazole, luliconazole, butoconazole, oxiconazole, or a combination thereof. Those having ordinary skill in the art may select other functionalized imidazole(s) if desired, but may find that the use of the above mentioned functionalized imidazole(s) such as miconazole is particularly beneficial.

The concentration of the functionalized imidazole(s) in the antifungal component of the compositions of the present application may be between about 1.0 mass % and about 10.0 mass % of the total mass of the composition, such as between about 2.0 mass % and about 3.0 mass %, for example, about 2.5 mass %.

According to various embodiments, the compositions of the present application may further optionally include at least one pharmaceutically acceptable penetration enhancing compound which may be selected by those having ordinary skill in the art. Non-limiting examples of penetration enhancing compounds that can be used include ibuprofen and $\beta$-cyclodextrin. The concentration of the penetration enhancing compound(s) in the compositions of the present application may be between about 1.0 mass % and about 5.0 mass % of the total mass of the composition, for example, about 2.0 mass % for ibuprofen and between about 0.5 mass % and about 10.0 mass % of the total mass of the composition, for example, about 1.0 mass % for $\beta$-cyclodextrin.

Other additives can be optionally used in the compositions of the present application, if desired. For example, the compositions may further optionally include at least one pharmaceutically acceptable anti-microbial agent, which may serve as a preservative, for example, benzyl alcohol.

According to further embodiments, the compositions of the present invention are generally acidic and may have a pH ranging between about 2.0 and about 6.5 (i.e., 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, or 6.5), with the understanding that any value of the pH that is within the mentioned limits is explicitly considered being within the scope of the invention. In various embodiments, the compositions of the present invention have a pH in the range of between about 2.5 and about 5.5, for example, between about 3.0 and about 4.0. In various embodiments, the compositions of the present invention have a pH of about 4.0.

According to further embodiments, methods for fabricating the above-described pharmaceutical compositions are provided. A one-batch formulation method may be used, where the components of the pharmaceutical formulation are combined in single container; each of the components may be added to the container simultaneously or consecutively. In one exemplary, non-limiting procedure, quantities of compounds comprising the antifungal component, a quantity of penetration enhancing compound(s), and a quantity of the excipient may be placed into a mixing container followed by mixing.

The resulting product may then be adapted for topical administration, for example, be formulated as a liquid, or alternatively, as a cream, gel, or ointment according to methods known to those having ordinary skill in the art. For example, if the composition is cream- or gel-based, such cream bases as RECURA™ Cream (Humco Corp. Austin, Tex.), LIPODERM® (Professional Compounding Centers of America (PCCA) Houston, Tex.)), LipoCream (Medisca, Inc., St. Laurent, Quebec, Canada), PENTRAVAN® (Fagron, Inc., Sty. Paul, Minn.), or Liposome Cream (Letco Medical, Decatur, Ala.) may be used. Those having ordinary skill in the art may selected different cream or gel bases if desired.

It will be understood by those having ordinary skill in the art that the specific dose levels and frequency of administration for any particular patient may be varied and will depend upon a variety of factors including the activity of the specific compound employed, the metabolic stability and length of action of that compound, the age, body weight, general health, gender, diet, and the severity of the particular inflammatory skin disease, disorder or pathology being treated.

In additional embodiments, pharmaceutical kits are provided. The kit includes a sealed container approved for the storage of pharmaceutical compositions, and the above-described pharmaceutical composition. An instruction for the use of the composition and the information about the composition are to be included in the kit. In various embodiments, the kit may also include a delivery device such as a brush, which may also be stored in the container.

The following examples are provided to further elucidate the advantages and features of the present invention, but are not intended to limit the scope of the invention. The examples are therefore for illustrative purposes only. USP pharmaceutical grade products were used in preparing the formulations described below.

Example 1

Preparing a Pharmaceutical Composition of the Invention

A pharmaceutical composition was prepared as described below. The following products were used in the amounts and concentrations specified:
(1) about 1.5 g of terbinafine hydrochloride powder;
(2) about 3.0 g of fluconazole powder;
(3) about 1.0 g of clotrimazole powder;
(4) about 1.8 g of ibuprofen powder;
(5) about 1.0 g of O-cyclodextrin powder;
(6) about 10.0 mL of anhydrous 200 proof ethanol;
(7) about 20.0 mL of benzyl alcohol; and
(8) about 100.0 mL of propylene glycol, q.s.

To obtain the composition, ethanol, benzyl alcohol and about 60% of propylene glycol were combined in a glass beaker with a spin bar. The powders, except β-cyclodextrin (i.e., terbinafine hydrochloride, fluconazole, clotrimazole, and ibuprofen), were slowly added to the beaker one by one while mixing using the spin bar, until completely dissolved. With continued mixing, β-cyclodextrin was then added and the mixing was continued until the solution thickened. The solution was then poured into 15 mL glass bottles equipped with nail brush applicators and labels warning that the product is for external use only were affixed to the bottles.

Example 2

Preparing a Cream-Based Pharmaceutical Composition of the Invention

A pharmaceutical composition may be prepared as described below. The following products may be used in the amounts and concentrations specified:
(1) about 3.0 g of terbinafine hydrochloride powder;
(2) about 10.0 g of fluconazole powder;
(3) about 10.0 g of clotrimazole powder;
(4) about 20.0 mL of propylene glycol; and
(5) about 100.0 g of RECURA™ Cream.

To obtain the composition, all the components (1)-(5) described above may be combined in an ointment jar, thoroughly mixed using an electric mortar and pestle, and then removed from the jar and milled twice. The composition may then be returned to the jar and mixed for one additional minute and dispensed into an appropriate container having the affixed labels warning that the product is for external use only.

Although the invention has been described with reference to the above examples, it will be understood that modifications and variations are encompassed within the spirit and scope of the invention. Accordingly, the invention is limited only by the following claims.

What is claimed is:

1. A pharmaceutical composition for treating, mitigating or preventing fungal nail diseases, disorders or pathologies, the composition consisting of:
   (a) a therapeutically effective quantity of an antifungal component consisting of:
      (a1) at least one functionalized allylamine compound;
      (a2) at least one functionalized triazole compound; and
      (a3) at least one functionalized imidazole compound;
   (b) a therapeutically effective quantity of at least one pharmaceutically acceptable penetration enhancing compound selected from the group consisting of ibuprofen and β-cyclodextrin; and
   (c) at least one pharmaceutically acceptable excipient that is compatible with the antifungal component and the penetration enhancing compound, wherein the pharmaceutically acceptable excipient is selected from group consisting of glycol and benzyl alcohol,
   wherein the composition has a pH in a range between about 2.0 and 6.5, and wherein the composition is formulated in a form that is suitable for topical administration.

2. The composition of claim 1, wherein the functionalized allylamine compound is selected from the group consisting of terbinafine, amorolfin, butenafine, flunarizine naftifine, and pharmaceutically suitable salts or hydrates thereof.

3. The composition of claim 2, wherein the functionalized allylamine compound is terbinafine.

4. The composition of claim 1, wherein the functionalized triazole compound is selected from the group consisting of fluconazole, isavuconazole, itraconazole, terconazole, voriconazole, albaconazole, efinaconazole, epoxiconazole, propiconazole, ravuconazole, posaconazole, and pharmaceutically suitable salts or hydrates thereof.

5. The composition of claim 4, wherein the functionalized triazole compound is fluconazole.

6. The composition of claim 1, wherein the functionalized imidazole compound is selected from the group consisting of miconazole, ketoconazole, clotrimazole, sertaconazole, sulconazole, tioconazole, fenticonazole, isoconazole, bifonazole, econazole, omoconazole, luliconazole, butoconazole, oxiconazole, and pharmaceutically suitable salts or hydrates thereof.

7. The composition of claim 6, wherein the functionalized imidazole compound is miconazole.

8. The composition of claim 1, wherein the antifungal component consists of terbinafine, fluconazole, and miconazole.

9. The composition of claim 1, wherein the glycol is propylene glycol.

10. The composition of claim 1, wherein the composition is in the form of a topical cream, a gel or an ointment.

11. The composition of claim 1, wherein the composition has a pH of about 2.5 to 5.5.

12. The composition of claim 11, wherein the composition has a pH of about 3.0 to 4.0.

13. The composition of claim 12, wherein the composition has a pH of about 4.0.

14. The composition of claim 8, wherein the composition has a pH of about 4.0.

15. A kit, comprising the pharmaceutical composition of claim 1, a container for housing the pharmaceutical composition, a delivery device, and instructions for use.

* * * * *